US012787959B2

(12) United States Patent
Brusca

(10) Patent No.: US 12,787,959 B2
(45) Date of Patent: Nov. 10, 2026

(54) TETRAPLOID WATERMELON LINE 54WA016

(71) Applicant: SYNGENTA CROP PROTECTION AG, Basel (CH)

(72) Inventor: James P. Brusca, Davis, CA (US)

(73) Assignee: SYNGENTA CROP PROTECTION AG, Basel (CH)

( * ) Notice: Subject to any disclaimer, the term of this patent is extended or adjusted under 35 U.S.C. 154(b) by 130 days.

(21) Appl. No.: 18/907,697

(22) Filed: Oct. 7, 2024

(65) Prior Publication Data

US 2026/0096523 A1 Apr. 9, 2026

(51) Int. Cl.

*A01H 5/10* (2018.01)
*A01H 5/08* (2018.01)
*A01H 6/34* (2018.01)

(52) U.S. Cl.

CPC ............... *A01H 6/342* (2018.05); *A01H 5/08* (2013.01)

(58) Field of Classification Search

None

See application file for complete search history.

(56) References Cited

U.S. PATENT DOCUMENTS 11,229,175 B2 * 1/2022 Kinkade ................ A01H 6/342

OTHER PUBLICATIONS

"Applying for a Plant Variety Certificate of Protection", USDA https://www.ams.usda.gov/services/pv po/application-help/apply, accessed May 1, 2023.*

UPOV, Explanatory Notes on Essentially Derived Varieties Under the 1991 Act of the UPOV Convention, Apr. 6, 2017, See Notes 14 and 30.*

Ex Parte C, USPQ 2d 1492 (1992).*

Ex Parte McGowen, Board Decision in U.S. Appl. No. 14/996,093, decided Jun. 15, 2020.*

Haun et al., 2011, Plant Physiol., 155:645-655.*

Großkinsky et al., 2015, J. Exp. Bot., 66:5429-5440.* us pvp Certificate No. 201000270, Issued Dec 10, 2010, '4XASSS4'.

* cited by examiner

*Primary Examiner* — Jason Deveau Rosen

(74) *Attorney, Agent, or Firm* — Karen A. Magri

(57) ABSTRACT

The present invention provides novel watermelon line 54WA016 and plant parts, seed, and tissue culture therefrom. The invention also provides methods for producing a watermelon plant by crossing the watermelon plants of the invention with themselves or another watermelon plant. The invention also provides watermelon plants produced from such a crossing as well as plant parts, seed, and tissue culture therefrom. Further provided are methods of producing triploid watermelon seed and plants and seedless watermelon fruit produced therefrom as well as the triploid watermelon seed and plants and the seedless fruits produced by such methods.

36 Claims, No Drawings

TETRAPLOID WATERMELON LINE 54WA016

FIELD OF THE INVENTION

This invention is in the field of watermelon plants, in particular, the invention relates to a novel tetraploid watermelon line, which can be used to produce triploid seeds and plants for production of seedless watermelon fruit.

BACKGROUND OF THE INVENTION

This invention relates to a new inbred tetraploid watermelon line, designated 54WA016.

Watermelon (*Citrullus lanatus*) is an important agricultural crop in the Cucurbitaceae family. According to the Food and Agricultural Organization of the United Nations (FAO), in 2023 there were 3.1 million hectares of watermelon grown worldwide, producing 77.5 million tons of fruit. Asia is by far the most important watermelon production region, with China accounting for most of the production. According to the USDA, in 2022 watermelon was grown on approximately 38,000 hectares in the United States. Florida, Georgia, Texas and California, having long warm growing seasons, were the top producing states. In the United States, watermelon consumption in 2021 was 6.53 kilograms per capita.

Triploid seedless watermelons have been commercially grown in the United States since the late 1980s. In recent decades, there has been an increase in consumer demand for seedless watermelons, and production of seedless watermelon has increased significantly. Currently, over 90% of the watermelons produced in the United States are triploid seedless watermelons. Seedless watermelon fruit receives well above the average price for seeded watermelons in the market. Triploid seedless watermelons also produce higher yields as compared with diploid seeded watermelons.

Triploid seedless watermelon is a sterile F1 hybrid between a tetraploid watermelon, as the female parent, and a diploid watermelon, as the male parent (Kihara, H. 1951, Triploid Watermelons, Proceedings of American Society for Horticultural Science, 58:217-230). Diploid watermelons have 22 chromosomes (2N=2X=22) in their somatic cells, and tetraploid watermelons have 44 chromosomes (2N=4X=44) in their somatic cells. Cells with three sets of homologous chromosomes are said to be triploid and are designated as 3X. When female flowers of tetraploid watermelon plants are cross-pollinated by the male flowers of diploid watermelon plants, the fruits produced by the tetraploid plants contain triploid F1 seeds that produce triploid plants. These triploid watermelon plants have 33 chromosomes (2N=3X=33) in their somatic cells. When the triploid plants are pollinated by a diploid plant acting as a male (e.g., cultivated together with diploid plants in the same field), the triploid plants are sterile and cannot produce mature seeds, thereby producing triploid seedless watermelon fruits. Typically, seedless watermelons contain some small edible white ovules, similar to those in immature cucumbers.

Watermelon in general, and seedless watermelon in particular, is an important and valuable vegetable crop. Thus, there is an ongoing need for improved inbred tetraploid watermelon lines.

SUMMARY OF THE INVENTION

According to the invention, there is provided a novel inbred tetraploid watermelon line designated 54WA016, characterized by producing mature fruits having a pink flesh color and having resistances to *Fusarium* Wilt race 1 and Anthracnose race 1. The invention also encompasses the seeds of watermelon line 54WA016, the plants of watermelon line 54WA016, plant parts of the watermelon line 54WA016 (including fruit, seed, gametes, scion, rootstock, shoots), methods of producing seed from watermelon line 54WA016, and methods for producing a watermelon plant by crossing the watermelon line 54WA016 with itself or another watermelon plant, methods for producing a watermelon plant containing in its genetic material one or more transgenes and/or locus conversions, and the transgenic and/or converted watermelon plants produced thereby. The invention also relates to methods for producing other watermelon plants derived from watermelon line 54WA016 and to watermelon plants, parts thereof and seed produced using those methods. The present invention further relates to hybrid watermelon seeds and plants (and parts thereof including fruit) produced by crossing watermelon line 54WA016 with another watermelon plant, e.g., hybrid triploid seeds and plants produced by crossing watermelon line 54WA016 with a diploid plant.

In another aspect, the present invention provides regenerable cells for use in tissue culture of watermelon line 54WA016. In embodiments, the tissue culture is capable of regenerating plants having all or essentially all of the physiological and morphological characteristics of the foregoing watermelon plant and/or of regenerating plants having the same or substantially the same genotype as the foregoing watermelon plant. In embodiments, the regenerated plant is a tetraploid plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules, rootstock, scion and/or seeds as well as callus and/or protoplasts derived from any of the foregoing. Still further, the present invention provides watermelon plants regenerated from the tissue cultures of the invention.

In representative embodiments, an exemplary watermelon plant according to the invention comprises cells comprising at least one set of chromosomes of watermelon line 54WA016. In embodiments, the watermelon plant is a tetraploid plant. In embodiments, the watermelon plant is a triploid plant. In embodiments, the watermelon plant is a diploid plant. Optionally, the watermelon plant can be an inbred plant or a hybrid plant.

As a further aspect, the invention provides a method of producing watermelon seed, the method comprising crossing a plant of watermelon line 54WA016 with itself or a second watermelon plant and allowing seed to form (e.g., tetraploid or triploid hybrid seed). Optionally, the method further comprises collecting the seed. In embodiments, the second watermelon plant is a diploid or tetraploid watermelon plant.

Another aspect of the invention provides methods for producing hybrid and other watermelon plants derived from watermelon line 54WA016. Watermelon plants derived by use of these methods are also part of the invention as well as plant parts, seed, gametes and tissue culture from such hybrid or derived watermelon plants.

In embodiments, a watermelon plant or population of watermelon plants derived from watermelon line 54WA016 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from watermelon line 54WA016, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 54WA016, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and/or double haploid technology. In embodiments, the derived watermelon plant is a tetraploid plant. In embodiments, the derived watermelon plant is a triploid plant. In embodiments, the derived watermelon plant is a diploid plant. Optionally, the watermelon plant can be an inbred plant, hybrid plant or double haploid plant. In embodiments, the watermelon plant derived from watermelon line 54WA016 is one, two, three, four, five or more breeding crosses removed from watermelon line 54WA016.

In embodiments, a hybrid or derived plant from watermelon line 54WA016 comprises a desired added trait(s). In representative embodiments, a watermelon plant derived from watermelon line 54WA016 comprises all of the morphological and physiological characteristics of watermelon line 54WA016 (e.g., as described in Table 1). In embodiments, the watermelon plant derived from watermelon line 54WA016 comprises an additional desired added trait(s) and otherwise all or essentially all of the morphological and physiological characteristics of watermelon line 54WA016 (e.g., as described in Table 1). In embodiments, the plant derived from line 54WA016 is a tetraploid plant. In embodiments, the plant derived from line 54WA016 is a triploid plant. In embodiments, the plant derived from line 54WA016 is a diploid plant. Optionally, the watermelon plant can be an inbred plant, a hybrid plant, or a double haploid plant.

The invention also relates to methods for producing a watermelon plant comprising in its genetic material one or more transgenes and to the transgenic watermelon plant produced by those methods (and progeny watermelon plants comprising the transgene). Also provided are plant parts, seed and tissue culture from such transgenic watermelon plants, optionally wherein one or more cells in the plant part, seed, or tissue culture comprises the transgene. The transgene can be introduced via plant transformation or breeding techniques (e.g., conventional breeding from an initial transformed plant(s)).

In another aspect, the present invention provides for converted plants of watermelon line 54WA016, which can optionally be a diploid, triploid or tetraploid plant, and comprising a single locus conversion (i.e., one or more single locus conversions). Plant parts, seed, and tissue culture from such converted plants are also contemplated by the present invention. A single locus conversion may be a dominant, semi-dominant or recessive allele. In representative embodiments, the single locus confers a trait such as, without limitation, male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, enhanced nutritional quality, improved appearance (e.g., color), improved salt tolerance, industrial usage, or any combination thereof. A single converted locus may be a naturally occurring watermelon locus, a genome edited locus, a mutated locus, or a transgene introduced into watermelon through genetic engineering techniques.

The invention further provides methods for developing watermelon plants (e.g., diploid, triploid or tetraploid) in a watermelon plant breeding program using plant breeding techniques including, for example, recurrent selection, backcrossing, pedigree breeding, double haploid techniques, restriction fragment length polymorphism enhanced selection, genetic marker enhanced selection, genome editing and/or transformation. Seeds, watermelon plants, and parts thereof, produced by such breeding methods are also part of the invention.

The invention also provides methods of multiplication or propagation of watermelon plants of the invention, which can be accomplished using any method known in the art, for example, via vegetative propagation, grafting and/or seed.

Additional aspects of the invention include harvested products and processed products from the watermelon plants of the invention. A harvested product can be a whole plant or any plant part, as described herein. Thus, in some embodiments, a non-limiting example of a harvested product includes a seed, a fruit (e.g., including the flesh and/or rind), a rootstock, a scion and/or a shoot.

In representative embodiments, a processed product includes, but is not limited to: cut, sliced, ground, pureed, dried, canned, jarred, washed, packaged, pickled, juiced, refrigerated, frozen, heated and/or cooked fruit or parts thereof (including the fruit flesh and/or rind) of the watermelon plants of the invention, or any other part thereof. In embodiments, the processed product includes sliced fruit (or parts thereof, e.g., the fruit flesh with or without the rind) of the invention. In embodiments, the processed product comprises juice from the fruit flesh, which may optionally be refrigerated or frozen.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of watermelon line 54WA016.

As a further aspect, the invention provides a plant of watermelon line 54WA016.

As an additional aspect, the invention provides a watermelon plant, or a part thereof, having all or essentially all of the physiological and morphological characteristics of a plant of watermelon line 54WA016. Optionally, the plant having all or essentially all of the physiological and morphological characteristics of a plant of watermelon line 54WA016 is a tetraploid plant.

The invention also provides plants that are diploid reversions of tetraploid watermelon line 54WA016 and parts (including seed and fruits) thereof. Also provided are methods of producing a diploid reversion derived from watermelon line 54WA016.

Further provided are methods of producing a diploid reversion of a tetraploid watermelon plant of the invention. In embodiments, the method comprises crossing two plants of watermelon line 54WA016 or selfing watermelon line 54WA016, harvesting seed, and growing a diploid reversion from the harvested seed. In embodiments, the fruit and/or seed of the diploid reversion is collected. Optionally, the diploid reversion can be used in a watermelon breeding program. For example, the diploid reversion can be crossed with itself or another diploid watermelon plant to produce a further watermelon plant, fruit and seed derived from watermelon line 54WA016. In embodiments, the method further comprises doubling the chromosomes of the diploid reversion (or a diploid watermelon progeny thereof) to produce a tetraploid watermelon plant.

The invention further provides triploid watermelon seed and triploid watermelon plants (and parts thereof, such as seedless fruit) produced by crossing watermelon line 54WA016 with a diploid plant. Optionally, 54WA016 is used as the female parent.

As another aspect, the invention provides fruit and/or seed of the watermelon plants of the invention and a processed product from the fruit and/or seed of the inventive watermelon plants.

As still another aspect, the invention provides a method of producing watermelon seed, the method comprising crossing a watermelon plant of the invention with itself or a second watermelon plant. In embodiments, the method is practiced to produce seeds of line 54WA016 (e.g., seed increase) by crossing the plant with itself, e.g., by open pollination of the variety. The invention also provides seed produced by this method and plants, and parts thereof including fruit, produced by growing the seed.

As yet a further aspect, the invention provides a method for producing a seed of a watermelon plant derived from watermelon line 54WA016, the method comprising: (a) crossing a watermelon plant of watermelon line 54WA016 with a second (different) watermelon plant; and (b) allowing seed of a watermelon plant derived from watermelon line 54WA016 to form. In embodiments, the method further comprises: (c) growing a plant from the seed derived from watermelon line 54WA016 of step (b); (d) selfing the plant of step (c) or crossing it to a second watermelon plant to form additional watermelon seed derived from watermelon line 54WA016, and (e) optionally repeating steps (c) and (d) one or more times to generate further derived watermelon seed from watermelon line 54WA016, wherein in step (c) a plant is grown from the additional watermelon seed of step (d) in place of growing a plant from the seed of step (b). In embodiments, the method comprises: (e) repeating steps (c) and (d) one or more times (e.g., one to three, one to five, one to six, one to seven, one to ten, three to five, three to six, three to seven, three to eight or three to ten times) to generate further derived watermelon seed. As another option, the method can comprise collecting the seed. The invention also provides seed (e.g., tetraploid, triploid or diploid) produced by these methods and watermelon plants produced by growing the seed, which can optionally be inbred or hybrid plants.

The invention further contemplates grafted watermelon plants and methods of producing a grafted watermelon plant, where watermelon line 54WA016 can be used as either the rootstock or the scion. Further encompassed by the invention are methods of producing grafted watermelon plants between line 54WA016 and a second different watermelon plant, where watermelon line 54WA016 can be used as either the rootstock or the scion.

Still further, as another aspect, the invention provides a method of vegetatively propagating a plant of watermelon line 54WA016, e.g., via shoot proliferation and then rooting in tissue culture. Detailed methods were described by Zhang et al. (Zhang, X. P., B. B. Rhodes, H. T. Skorupska, W. C. Bridges. 1995. Generating Tetraploid Watermelon Using Colchicine in Vitro. G. Lester & J. Dunlap et al. (eds.), Cucurbitaceae' 94: 134-139). In a non-limiting example, the method comprises: (a) collecting tissue capable of being propagated from a plant of watermelon line 54WA016; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of introducing a desired added trait into watermelon line 54WA016, the method comprising: (a) crossing a first plant of watermelon line 54WA016 with a second watermelon plant (e.g., a tetraploid plant) that comprises a desired trait to produce $F_1$ progeny; (b) selecting an $F_1$ progeny that comprises the desired trait; (c) crossing the selected $F_1$ progeny with watermelon line 54WA016 to produce backcross progeny; and (d) selecting backcross progeny comprising the desired trait to produce a plant derived from watermelon line 54WA016 comprising a desired trait.

In embodiments, the selected progeny produces a fruit with the characteristics of line 54WA016 as described herein. In embodiments, the selected progeny comprises all or essentially all the morphological and physiological characteristics of watermelon line 54WA016 (e.g., a described in Table 1). Optionally, the method further comprises: (e) repeating steps (c) and (d) one or more times (e.g., one to three, one to five, one to six, one to seven, one to ten, three to five, three to six, three to seven, three to eight or three to ten times) to produce a plant derived from watermelon line 54WA016 comprising the desired trait, wherein in step (c) the selected backcross progeny produced in step (d) is used in place of the selected F1 progeny of step (b). In embodiments, the plant derived from line 54WA016 and comprising the desired added trait is a tetraploid plant. In embodiments, the plant derived from line 54WA016 and comprising the desired added trait is a triploid plant. In embodiments, the plant derived from line 54WA016 and comprising the desired added trait is a diploid plant.

In representative embodiments, the invention also provides a method of producing a plant of watermelon line 54WA016 comprising a desired added trait, the method comprising introducing a transgene conferring the desired trait into a plant of watermelon line 54WA016. The transgene can be introduced by transformation methods (e.g., genetic engineering) or breeding techniques (e.g., crossing 54WA016 with a transformed plant or a plant that is descended from a transformed plant and comprises the transgene). In embodiments, the plant comprising the transgene produces a mature fruit with the characteristics of line 54WA016 described herein. In embodiments, the plant comprising the transgene comprises all or essentially all morphological and physiological characteristics of watermelon line 54WA016 (e.g., as described in Table 1).

The invention also provides watermelon plants (e.g., a diploid, triploid or tetraploid watermelon plant) produced by the methods of the invention, wherein the watermelon plant has the desired added trait as well as seed and fruits from such watermelon plants. The invention also provides seed that produces the plants derived from line 54WA016 and comprising a desired added trait.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, a watermelon plant of the invention (including transgenic plants, converted plants, hybrid plants and watermelon plants derived from watermelon line 54WA016, and plants produced by the methods of the invention) are characterized by, e.g., one or more of tetraploidy, mature fruits having a pink flesh color and/or having resistance to *Fusarium* Wilt race 1 and/or Anthracnose race 1. In representative embodiments, transgenic plants, converted plants, hybrid plants and watermelon plants derived from watermelon line 54WA016, and plants watermelon plant produced by the methods of the invention comprise at least 3, 4, 5, 6, 7, 8, 9, 10 or more of the morphological and physiological characteristics of watermelon line 54WA016 described herein (e.g., as described in Table 1), or even all of the morphological and physiological characteristics of watermelon line 54WA016, so that said plants are not significantly different for said traits than watermelon line 54WA016, as determined at the 5% significance level when grown in the same environmental conditions; optionally, with the presence of one or more desired additional traits (e.g., male sterility, disease resistance, pest or insect resistance, herbicide resistance, and the like).

As a further aspect, the invention provides a method of producing triploid watermelon seed, the method comprising: (a) crossing a watermelon plant of line 54WA016 with a diploid watermelon plant; and (b) optionally, harvesting the resultant triploid watermelon seed. In embodiments, the plant of line 54WA016 is the female parent and the diploid parent is the male plant (i.e., pollinator). Also provided is a hybrid triploid watermelon seed produced by the foregoing method, and a triploid watermelon plant (and parts thereof, including seedless fruit) grown from the triploid seed.

The invention also provides as another aspect, a method of producing seedless watermelon fruit, the method comprising: (a) crossing the triploid watermelon plant produced by the method of the preceding paragraph and a diploid watermelon plant; (b) allowing a seedless fruit to form; and (c) optionally, harvesting the seedless fruit. Also provided is a seedless watermelon fruit produced by the foregoing method.

As still a further aspect, the invention provides a tetraploid watermelon plant, or a part thereof, produced by crossing a 54WA016 plant with a different tetraploid watermelon plant (e.g., a tetraploid inbred or hybrid plant).

The invention further provides a method of developing a tetraploid watermelon line in a watermelon plant breeding program using plant breeding techniques, which include employing a watermelon plant, or a part thereof, as a source of plant breeding material, the method comprising: (a) obtaining the watermelon plant, or a part thereof, of line 54WA016 as a source of breeding material; and (b) applying plant breeding techniques.

The invention also encompasses plant parts, plant material, pollen, ovules, leaves, fruit and seed from the watermelon plants of the invention. The invention also provides seed that produces the watermelon plants of the invention. Also provided is a tissue culture of regenerable cells from the watermelon plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are watermelon plants regenerated from a tissue culture of the invention.

In still yet another aspect, the invention provides a method of determining a genetic characteristic of watermelon line 54WA016 or a progeny thereof, e.g., a method of determining a genotype of watermelon line 54WA016 or a progeny thereof using molecular genetic techniques. In embodiments, the method comprises detecting in the genome of a 54WA016 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

The present invention is based, in part, on the development of a novel watermelon characterized by producing mature fruits having a pink flesh color and having resistances to *Fusarium* Wilt race 1 and Anthracnose race 1.

Those skilled in the art will appreciate that when a comparison of physiological and morphological characteristics between two or more varieties is made, it is assumed that the varieties are grown under the same environmental conditions, whether in the field or green house. In addition, such comparisons are generally made on the basis of observations taken on a population of plants.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions.

In the description that follows, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents (the "recurrent" parent), for example, a first generation $F_1$ hybrid with one of the parental genotypes of the $F_1$ hybrid, e.g., backcrossing 1, 2, 3, 4, 5, 6, 7, 8, 9, or more times to the recurrent parent. The other parental plant is termed the "nonrecurrent" parent, which may also be referred to as the "donor" parent if it contributes a gene(s) for a desired characteristic.

"Cotyledon". One of the first leaves of the embryo of a seed plant; typically one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1N chromosomes. The chromosomes in these plantlets are then induced to "double" (e.g., using chemical means) resulting in cells containing 2N chromosomes. The progeny of these plantlets are termed "double haploid" and are essentially not segregating any more (e.g., are stable). The term "double haploid" is used interchangeably herein with "dihaploid."

"Essentially all the physiological and morphological characteristics". A plant having "essentially all the physiological and morphological characteristics" (and similar phrases) means a plant having all of the desired physiological and morphological characteristics of variety 54WA016, except for the characteristic(s) derived from a converted locus/loci (e.g., one or more single converted loci), for example, introduced via backcrossing to variety 54WA016, a modified gene(s) resulting from genome editing techniques, an introduced transgene (i.e., introduced via genetic transformation techniques), or mutation, when both plants are grown under the same environmental conditions. In embodiments, a plant having "essentially all of the physiological and morphological characteristics" means a plant having all of the characteristics of the reference plant with the exception of five or fewer traits, 4 or fewer traits, 3 or fewer traits, 2 or fewer traits, or one trait. In embodiments, a plant comprising "essentially all of the physiological and morphological characteristics" of variety 54WA016 produces a mature fruit having a pink flesh color and having resistances to *Fusarium* Wilt race 1 and Anthracnose race 1, and is optionally diploid or tetraploid. In embodiments, a plant comprising "essentially all of the physiological and morphological characteristics" of variety 54WA016 comprises the traits set forth in Table 1.

"Gene". As used herein, "gene" refers to a segment of nucleic acid comprising an open reading frame. A gene can be introduced into a genome of a species, whether from a different species or from the same species, using transformation or various breeding methods.

"Inbred line": As used herein, the phrase "inbred line" refers to a genetically homozygous or nearly homozygous population. An inbred line, for example, can be derived through several cycles of sib crossing and/or selfing and/or via double haploid production. In embodiments, inbred lines breed true for one or more traits of interest. An "inbred plant" or "inbred progeny" is an individual sampled from an inbred line.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, rootstock, scion, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, rootstocks, scions, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, shoot, stem, stalk, petiole, pith, capsule, a scion, a rootstock and/or a fruit including callus and protoplasts derived from any of the foregoing.

"Quantitative Trait Locus". A Quantitative Trait Locus (QTL) refers to a genetic locus that controls to some degree, numerically representable traits that are usually continuously distributed (i.e., a quantitative trait).

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., environmental, including cold, drought, heat, high salinity) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. Generally, a watermelon plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus conversion". Refers to a modification at a single locus in a plant that confers a trait (e.g., a trait of interest), such as without limitation disease resistance, fertility, sterility, enhanced flowering, and the like.

"Single locus converted plant". A single locus converted or conversion plant (and similar terms) refers to a plant that comprises a single locus conversation, which may be introduced by any suitable method known in the art, e.g., by plant breeding techniques (e.g., backcrossing), genome editing techniques, genetic transformation techniques and/or mutation techniques wherein the converted plant comprises the trait conferred by the single locus introduced into the plant and otherwise all or essentially all of the morphological and physiological characteristics of the parent plant (e.g., line).

As used herein, a "small" watermelon fruit refers to a mean fruit weight that is less than about 8 kg, 7 kg, 6 kg, 5 kg, 4.5 kg or even 4 kg.

"Substantially equivalent characteristic". A characteristic that, when compared, does not show a statistically significant difference (e.g., p=0.05) from the mean.

"Thousand seed weight" as used herein refers to the average weight of 1000 seeds of the variety. In embodiments, the plant or variety has a "low" or "relatively low" thousand seed weight, e.g., less than about 55, 50, 45, 44, 43, 42, 41 or 40 grams per thousand seeds (e.g., untreated seeds).

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context than is found in the native state (e.g., different genomic location and/or in operable association with exogenous regulatory elements such as a promoter). The transgene can comprise an open reading frame encoding a polypeptide or can encode a functional non-translated RNA (e.g., RNAi).

Botanical Description of the Watermelon Line 54WA016.

Characteristics. New watermelon inbred tetraploid line 54WA016 is characterized by producing mature fruits having a pink flesh color and having resistances to *Fusarium* Wilt race 1 and Anthracnose race 1.

Promising triploid hybrids produced using 54WA016 as female parent have been developed. 54WA016 is a new, unique and useful elite inbred tetraploid line for producing triploid seedless hybrids.

Tetraploid watermelon line 54WA016 is the result of a cross between two elite tetraploid lines 13180F and 4XDKFD55G (U.S. Pat. No. 9,402,347), followed by multiple generations of selfing and selection for desirable characteristics. Neither parent line is public variety or commercially available. Watermelon line 54WA016 has shown uniformity and stability within the limits of environmental influence. The variety has been increased with continued observation for uniformity. No variant traits have been observed or are expected in watermelon line 54WA016.

A more detailed botanical description of 54WA016 is shown in Table 1 below.

TABLE 1

Description of 54WA016 based on open field trials.

| Characteristic | 54WA016 |
|---|---|
| General fruit type: | Round large |
| Days to maturity: | 65 days |
| Maturity category: | Medium |
| Ploidy: | Tetraploid |
| Leaf shape: | Ovate |
| Leaf lobes: | Lobed |
| Leaf dorsal pubescence: | Yes |
| Leaf ventral pubescence: | Yes |
| Leaf color: | Medium green |
| Flower color: | Yellow |
| Mature fruit shape: | Round |
| Mature fruit length (cm): | 24.7 |
| Mature fruit diameter (midsection): | 24.1 |
| Mature fruit weight (kg): | 6.7 |
| Mature fruit surface: | Slight groove |
| Mature fruit skin color pattern: | Mottled |
| Mature fruit primary color: | Light Green |
| Mature fruit secondary color: | Medium green |
| Rind texture: | Tough |
| Rind thickness sides (cm): | 1.4 |
| Flesh texture: | Soft |
| Flesh coarseness: | Fine |
| Flesh color: | Pink |
| Seed length (mm): | 8.9 |
| Seed width (mm): | 7 |
| Seed thickness (mm): | 2.9 |
| Thousand seed weight (g): | 66.8 |
| Seed color: | Mottled brown |
| Anthracnose, race 1 (*Colletotrichum orbiculare*) | Intermediate resistance |
| Fusarium wilt, race 1 (*Fusarium oxysporum* f. sp. *Niveum*) | Intermediate resistance |

Tissue Culture.

In embodiments, watermelon plants can be propagated by tissue culture and regeneration. Tissue culture of various plant tissues and regeneration of plants therefrom is well known. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28 (2), 139-145 (1992). It is clear from the literature that the state of the art is such that these methods of obtaining plants are routinely used and have a high rate of success. Thus, another aspect of this invention is to provide cells which upon growth and differentiation produce watermelon plants having desired characteristics of watermelon line 54WA016 (e.g., one or more of the characteristics of the fruit of line 54WA016 as described herein). Optionally, watermelon plants can be regenerated from the tissue culture of the invention comprising all or essentially all of the physiological and morphological characteristics of watermelon line 54WA016.

As used herein, the term "tissue culture" indicates a composition comprising isolated cells of the same or a different type or a collection of such cells organized into parts of a plant. Exemplary types of tissue cultures comprise protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Tetraploid Watermelon Lines and Triploid Seed Production

In embodiments, tetraploid watermelons are used to make triploid hybrid watermelon seeds and plants that produce seedless fruit. In commercial production of triploid watermelon seed, tetraploid and diploid parental lines are typically planted in the same field. Cross-pollination between the tetraploid line, generally used as the female parental line, and the diploid line, typically the male parental line, are accomplished by either hand or bee pollination. Triploid watermelon seeds are produced in fruits of tetraploid plants that are fertilized with pollen of diploid plants. All commercially grown seeded watermelons are diploid; therefore, there are many diploid lines for use as diploid parents. The major limitation to development of seedless watermelon varieties lies in the availability of useful elite tetraploid parental lines.

Tetraploid watermelon lines can be developed from diploid lines by doubling the chromosomes of diploid watermelon lines using methods routine in the art. Chromosome doubling was first accomplished with the alkaloid colchicine by applying colchicine to the growing point of newly emerged watermelon seedlings. Tissue culture methods have also been developed (Zhang, X. P., B. B. Rhodes, H. T. Skorupska, W. C. Bridges, 1995, Generating Tetraploid Watermelon Using Colchicine in Vitro, G. Lester & J. Dunlap et al. (eds.), Cucurbitaceae' 94: 134-139). Dinitroanilines have been used to double chromosome numbers. Li et al. compared in vitro chromosome doubling effectiveness using colchicine and the dinitroanilines, ethalfluralin (N-ethyl-N-2-methyl-2-propenyl)-2,6-dinitro-4-(trifluoromethyl)benzanine), and oryzalin (3,5-dinitro-N4, N4-dipropylsulfanilamide) and concluded that either ethalfluralin or oryzalin was preferable to colchicine (Li, Ying, J. F. Whitesides, B. Rhodes, 1999, In vitro generation of tetraploid watermelon with two different dinitroanilines and colchicines, Cucurbit Genetics Cooperative Rpt 22:38-40).

Several treatment methods can be used to induce tetraploids from diploids using, for example, the chemicals mentioned above. One exemplary method is to treat the seeds before sowing. The seeds are soaked in clean water for 5-6 hrs and then in either a colchicine (0.2%) or dinitroanilines (e.g. 35 UM oryzalin) solution for 24 hrs. The seeds are briefly rinsed before sowing. Dry seed can also be directly soaked in the chemical solution without pre-soaking in the water. A second exemplary method comprises treating the newly emerged seedling. To illustrate, the diploid inbreds can be sown in the greenhouse in seedling flats. The soil temperature is kept at 29-31° C. for rapid and uniform germination. One drop of colchicine (0.1%) or dinitroanilines (e.g. 35 UM oryzalin) solution is added to the shoot apex between the cotyledons as soon as the seedling has emerged from soil. The solution can be applied to the growing point in the morning or evening for three consecutive days. Another illustrative method is to treat the shoot apex of germinated seed after which the germinated seed is planted into soil, and germinated in an incubator at 30° C. When the radicals are about 2 cm long, the portion above the hypocotyls of the germinated seeds is immersed upside down into colchicine (0.1%) or dinitroaniline solution (35 UM oryzalin) for 10-15 hrs at 30° C. in an incubator. The treatment is typically conducted in a high humidity chamber or box to assure that the radicals/roots are not desiccated. The seeds are then washed and planted in the soil. The last two methods, although more tedious to use, usually give better recovery of tetraploid events as the root system is not affected by the treatment.

The next step is to develop tetraploid lines from individual converting events. For example, the tetraploid individuals selected on the basis of morphological characteristics can be self-pollinated and the resulting seeds planted in the next generation as lines. These lines can again be self-pollinated and compared for fertility and horticultural traits. Desirable lines may be bulk harvested if there is no variation within the line and among selected lines. Further seed increases may be conducted in an isolation block. Mass selection may be conducted for this increase in the isolation plot and thereafter. Fertility of the tetraploid may be improved in subsequent generations.

The use of tissue culture to propagate tetraploid watermelon plants is exemplified in Adelberg, J. W., B. B. Rhodes, Micropropagation from zygotic tissue of watermelon, C. E. Thomas (ed.) Proc. of the Cucurbitaceae 89: Evaluation and enhancement of cucurbit germplasm, Charleston S.C., USA; and Zhang et al., Shoot regeneration from immature cotyledon of watermelon, Cucurbit Genetics Coop. 17:111-115 (1994).

Crossing two different tetraploids and then going through recombination breeding can also result in new tetraploid lines. A longer breeding period is typically employed to develop a stable tetraploid line using this approach because of the larger number of combinations and the fewer seeds that tetraploids produce. However, some breeders have made good progress by taking this approach.

Because meiosis is sometimes irregular in autotetraploids, there can be diploids (e.g., diploid reversions) and aneuploids among the offspring. The leaves, flowers and pollen grains of tetraploids are morphologically distinct from diploids (Zhang, X. P., B. B. Rhodes, H. T. Skorupska, W. C. Bridges, 1995, Generating Tetraploid Watermelon Using Colchicine in Vitro, G. Lester & J. Dunlap et al. (eds.), Cucurbitaceae' 94: 134-139). Tetraploids also have a different number of chloroplasts in the guard cells (Compton, M. E., D. J. Gray and G. W. Elmstrom. 1996, Identification of tetraploid regenerants from cotyledons of diploid watermelon cultures in vitro, Euphytica 87:165-172). These morphological traits can help the breeder eliminate the diploids and aneuploids occurring in the tetraploid population during sexual propagation. Diploid reversions can also be identified in situations in which a diploid derived from line 54WA016 is desired, and such diploid reversions are also encompassed by the present invention.

Accordingly, the invention contemplates as one aspect a method of producing triploid watermelon seed, the method comprising: (a) crossing the watermelon plant of line 54WA016 with a diploid watermelon plant; and (b) harvesting the resultant triploid watermelon seed. In embodiments the plant of line 54WA016 is the female parent and the diploid plant is the male parent. In embodiments, the plant of line 54WA016 is the male parent and the diploid plant is the female parent. The triploid watermelon seed produces a triploid plant, which when pollinated by a diploid watermelon plant as male produces a seedless watermelon fruit.

The invention further provides a method of producing seedless watermelon fruit, the method comprising: (a) crossing a triploid plant produced from line 54WA016 (e.g., an F1 hybrid of 54WA016 produced as described in the preceding paragraph) and a diploid watermelon plant; (b) allowing seedless fruit to form; and (c) optionally, harvesting the seedless fruit. In embodiments, the triploid watermelon seeds and seeds from a diploid plant are planted in one or more rows, and the plants are allowed to mature and develop seedless fruit. In embodiments, diploid and triploid seed are planted in the same row. In embodiments the triploid plant is the female parent and the diploid plant is the male parent. In embodiments, the triploid plant is the male parent and the diploid plant is the female parent.

Any suitable method can be used to produce triploid seeds from inbred 54WA016. Two commonly used methods are described below. Variations to these methods can be made according to the actual production situation.

Hand-Pollination Method

Hand pollination can be used for producing triploid seed from 54WA016. For example, in embodiments, the inbred tetraploid female parent 54WA016 and the inbred diploid male parent line are planted in the same field or greenhouse. To illustrate, in an exemplary method, the inbred male parent is planted 7-10 days earlier than the female parent 54WA016 to ensure adequate pollen supply at the pollination time. The male parent and female parent 54WA016 can be planted, for example, in the ratio of 1 male parent to 4-10 female parents. Pollination is generally started when the second female flower on the tetraploid female parent 54WA016 is ready to flower. Female flower buds that are ready to open the next day are identified, covered with paper cups or small paper bags that prevent bee or any other insect visits to the female flowers, and marked with any kind of material that can be easily seen the next morning. The male flowers of the diploid male parent are collected in the morning before they are open and visited by pollinating insects. The covered female flowers of the tetraploid female parent, which have opened, are uncovered and pollinated with the collected fresh male flowers of the diploid male parent, starting after the male flower sheds pollen. The pollinated female flowers are again covered after pollination to prevent bees and any other insect visits. The pollinated female flowers are also marked. Generally, only the marked fruits are harvested for extracting triploid hybrid seed.

Bee-Pollination Method

Bee pollination can also be used in triploid watermelon production. In an exemplary bee-pollination method, the tetraploid female parent 54WA016 and the diploid male parent are typically planted in a ratio of 2 tetraploid parents to 1 male parent (e.g., 2:1 rows in a field). Generally, all of the male flower buds on the female tetraploid parent plants are removed manually (the de-budding process) during the pollination season, typically on a daily basis. Beehives are placed in the field for transfer of pollen by bees from the male parent to the female flowers of the female parent. Fruits set during this de-budding time are marked. Generally, only the marked fruits are harvested for extracting hybrid triploid seed.

Additional Breeding Methods.

This invention is also directed to methods for producing a watermelon plant by crossing a first parent watermelon plant with a second parent watermelon plant wherein the first or second parent watermelon plant is a plant of watermelon line 54WA016. Further, both first and second parent watermelon plants can come from watermelon line 54WA016. Thus, any of the following exemplary methods using watermelon line 54WA016 are part of this invention: selfing, open pollinations, backcrosses, hybrid production, crosses to populations, double haploid production, and the like. All plants produced using watermelon line 54WA016 as at least one parent are within the scope of this invention, including those developed from watermelon plants derived from watermelon line 54WA016. Advantageously, watermelon line 54WA016 can be used in crosses with other, different, watermelon plants to produce first generation ($F_1$) watermelon hybrid seeds and plants with desirable characteristics. The watermelon plants of the invention can also be used for transformation where exogenous transgenes are introduced and expressed by the plants of the invention. Genetic variants created either through traditional breeding methods, genome editing, mutagenesis or through transformation of the cultivars of the invention by any of a number of protocols known to those of skill in the art are intended to be within the scope of this invention.

The following describes exemplary breeding methods that may be used with watermelon line 54WA016 in the development of further watermelon plants. One such embodiment is a method for developing watermelon line 54WA016 progeny watermelon plants in a watermelon plant breeding program comprising: obtaining a plant, or a part thereof, of watermelon line 54WA016, utilizing said plant or plant part as a source of breeding material, and selecting a watermelon line 54WA016 progeny plant, e.g., with molecular markers in common with watermelon line 54WA016 and/or with some, all or essentially all morphological and/or physiological characteristics of watermelon line 54WA016 (see, e.g., Table 1). In representative embodiments, the progeny plant has at least 1, 2, 3, 4, 5, 6, 7, 8, 9, 10 or more of the morphological and physiological characteristics of watermelon line 54WA016 described herein when grown under the same environmental conditions; optionally, with the presence of one or more desired additional traits (e.g., male sterility, disease resistance, pest or insect resistance, herbicide resistance, and the like). In embodiments, the progeny plant comprises all of the morphological and physiological characteristics of watermelon line 54WA016 so that said progeny watermelon plant is not significantly different for said traits than watermelon line 54WA016, as determined at the 5% significance level when grown in the same environmental conditions. Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of watermelon line 54WA016 progeny plants, comprising crossing watermelon line 54WA016 with another watermelon plant, thereby producing a population of watermelon plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 54WA016, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 54WA016. One embodiment of this invention is the watermelon plant produced by this method and that has at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 54WA016, and optionally may be the result of a breeding process comprising one or two breeding crosses and as a further option, one or more of selfing, sibbing, backcrossing and/or double haploid techniques in any combination and any order. In embodiments, the breeding process does not include a breeding cross, and optionally comprises selfing, sibbing, backcrossing and/or double haploid techniques.

One of ordinary skill in the art of plant breeding would know how to evaluate the traits of two plants to determine if there is, or is not, a significant difference between the two traits expressed by those varieties. For example, see Fehr and Walt, Principles of Cultivar Development, pp. 261-286 (1987). Thus, the invention includes watermelon line 54WA016 progeny watermelon plants characterized by the traits of 54WA016 described herein. In embodiments, the invention encompasses progeny plants having a combination of at least 2, 3, 4, 5, 6, 7, 8, 9, 10 or more of the characteristics as described herein for watermelon line 54WA016, so that said progeny watermelon plant is not significantly different for said traits than watermelon line 54WA016, as determined at the 5% significance level when grown in the same environmental conditions. Using techniques described herein and those known in the art, molecular markers may be used to identify said progeny plant as progeny of watermelon line 54WA016. Mean trait values may be used to determine whether trait differences are significant, and optionally the traits are measured on plants grown under the same environmental conditions (e.g., in the field or greenhouse).

Progeny of watermelon line 54WA016 may also be characterized through their filial relationship with watermelon line 54WA016, as for example, being within a certain number of breeding crosses of watermelon line 54WA016. A breeding cross is a cross made to introduce new genetics into the progeny, and is distinguished from a cross, such as a self or a sib cross or a backcross to 54WA016 as a recurrent parent, made to select among existing genetic alleles. The lower the number of breeding crosses in the pedigree, the closer the relationship between watermelon line 54WA016 and its progeny. For example, progeny produced by the methods described herein may be within 1, 2, 3, 4, 5 or more breeding crosses of watermelon line 54WA016.

In representative embodiments, a watermelon plant derived from watermelon line 54WA016 comprises cells comprising at least one set of chromosomes derived from watermelon line 54WA016.

In embodiments, a watermelon plant or population of watermelon plants derived from watermelon line 54WA016 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 54WA016, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 54WA016, and optionally may be the result of one or more of selfing, sibbing, backcrossing and/or double haploid techniques in any combination. In embodiments, the watermelon plant derived from watermelon line 54WA016 is one, two, three, four, five or more breeding crosses removed from watermelon line 54WA016.

In representative embodiments, a plant derived from watermelon line 54WA016 is a double haploid plant, a hybrid plant, an inbred plant, a tetraploid plant, a triploid plant and/or a diploid plant.

In embodiments, a derived plant from watermelon line 54WA016 comprises a desired added trait. In representative embodiments, a watermelon plant derived from watermelon line 54WA016 comprises the desired added trait and otherwise all or essentially all of the morphological and physiological characteristics of watermelon line 54WA016 (e.g., as described in Table 1).

According to the invention, tetraploid inbreds can be used as parental lines to develop new tetraploid lines. The unique and desirable traits of 54WA016 make it useful as a parental line in the development of new tetraploid inbreds. 54WA016 can be used as either female or male parent to cross with another tetraploid watermelon (e.g., an inbred or hybrid tetraploid) to develop new tetraploid inbreds, followed, e.g., by multiple rounds of selfing or a double haploid process to produce a new inbred tetraploid.

In embodiments, 54WA016 can be crossed with another tetraploid watermelon comprising a genetic locus/loci conferring a trait(s) of interest (e.g., disease resistance, male flowering, etc.). This can be followed by backcrossing to 54WA016, optionally to produce a converted watermelon plant comprising one or more desired added traits (e.g., one or more single locus conversion) and otherwise all of the physiological and morphological characteristics of 54WA016.

Those skilled in the art will appreciate that any of the traits described herein with respect to plant transformation methods can be introduced into a plant of the invention (e.g., watermelon line 54WA016 and hybrid watermelon plants and other watermelon plants derived therefrom) using breeding techniques.

Genetic Transformation.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as “transgenes.” Methods for producing transgenic plants are known in the art, and in particular embodiments the present invention also relates to transformed versions of watermelon plants disclosed herein.

Genetic engineering techniques can be used (alone or in combination with breeding methods) to introduce one or more desired added traits into a plant, for example, watermelon 54WA016 or progeny or watermelon plants derived thereof. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid and can be used alone or in combination with other plasmids, to provide transformed watermelon plants using transformation methods as described herein to incorporate transgenes into the genetic material of the watermelon plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation-Selectable markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase), selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation-Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissues are referred to as "tissue-specific." A "cell type" specific promoter preferentially drives expression in certain cell types in one or more organs, for example, vascular cells in roots or leaves. An "inducible" promoter is a promoter that is under environmental or exogenous control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and the foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a watermelon plant of the invention. In another embodiment, the biomass of interest is a watermelon seed and/or fruit.

Likewise, by means of the present invention, agronomic transgenes and other desired added traits can be expressed in transformed plants (and their progeny, e.g., produced by conventional breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to plant pests (e.g., nematode or insect) or disease (e.g., fungal, bacterial or viral), transgenes that confer herbicide tolerance, transgenes that confer male sterility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color and/or fruit flesh), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for genome editing techniques.

Any transgene, including those exemplified above, can be introduced into the watermelon plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include *agrobacterium*-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described herein) allows for preferential selection of transformed cells, tissues and/or plants, using regeneration and selection methods now well known in the art.

The foregoing methods for transformation are typically used to produce a transgenic watermelon line. The transgenic watermelon line can then be crossed with another (non-transgenic or transgenic) plant using conventional breeding techniques in order to produce a new transgenic watermelon line. In embodiments, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene.

Genome Editing.

Genome editing methodologies are known in the art and can be carried out by any suitable technique. For example, targeted genome editing can be done using CRISPR/Cas9 technology (Saunders & Joung, Nature Biotechnology, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. J. Bacteriol. 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. (Barrangou, R., et al. Science 315, 1709-1712 (2007)). Many plants have already been modified using the CRISPR system. See for example, U.S. Application Publication No. WO2014068346 (Gyorgy et al., Identification of a *Xanthomonas* euvesicatoria resistance gene from pepper (*Capsicum annuum*) and method for generating plants with resistance); Martinelli, F. et al., "Proposal of a Genome Editing System for Genetic Resistance to Tomato Spotted Wilt Virus" *American Journal of Applied Sciences* 2014; Noman, A. et al., "CRISPR-Cas9: Tool for Qualitative and Quantitative Plant Genome Editing" *Frontiers in Plant Science* Vol. 7 Nov. 2016; and "Exploiting the CRISPR/Cas9 System for Targeted Genome Mutagenesis in *Petunia*" *Science Reports* Volume 6: February 2016.

Genome editing can also be done using crRNA-guided surveillance systems for genome editing. Additional information about crRNA-guided surveillance complex systems for genome editing can be found in the following documents: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34:1473-1476. Therefore, the invention also contemplates using genome editing on watermelon line 54WA016 to modify traits of interest including without limitation disease resistance, insect resistance, nematode resistance, herbicide resistance, flowering, fertility, sterility, and the like.

Locus Conversion.

The term "locus converted plant", "converted plant", or plant having a "locus conversion" (and similar terms) as used herein refers to those plants that are developed, for example, by backcrossing, genome editing, genetic transformation and/or mutation (e.g., into a parental line), wherein essentially all of the desired morphological and physiological characteristics of a variety are recovered in addition to the one or more converted loci introduced into the plant. To illustrate, in particular embodiments, backcrossing into a parental line can be used with the present invention to improve or introduce a characteristic into the variety. The gene/locus that is transferred can be a native gene/locus, a mutated native gene/locus or a transgene introduced by genetic engineering techniques into the plant (or ancestor thereof). In a typical backcross protocol, the original variety of interest (recurrent parent) is crossed to a second variety (nonrecurrent parent) that carries the locus/loci of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred locus/loci and associated trait(s) from the nonrecurrent parent.

Genetic Analysis of Watermelon Line 54WA016.

The invention further provides a method of determining a genetic characteristic of watermelon line 54WA016 or a progeny thereof, e.g., a method of determining a genotype of watermelon line 54WA016 or a progeny thereof. In embodiments, the method comprises detecting in the genome of a 54WA016 plant, or a progeny plant thereof, at least a first polymorphism (e.g., by detecting a nucleic acid marker by a method comprising nucleic acid amplification and/or nucleic acid sequencing). To illustrate, in embodiments, the method comprises obtaining a sample of nucleic acids from the plant and detecting at least a first polymorphism (e.g., a Single Nucleotide Polymorphism [SNP]) in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT INFORMATION

Applicants have made a deposit of at least 625 seeds of watermelon line 54WA016 with the Provasoli-Guillard National Center for Marine Algae and Microbiota (NCMA) at Bigelow Laboratory for Ocean Sciences, 60 Bigelow Drive, East Boothbay, Me., 04544 U.S.A. under NCMA Accession No. 202411027 on Nov. 20, 2024 This deposit of watermelon variety 54WA016 will be maintained in the NCMA depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. During the pendency of this application, access to the deposited material will be afforded to the Commissioner on request. All restrictions on the availability of the deposited material from the NCMA to the public will be irrevocably removed upon granting of the patent. Applicants impose no restrictions on the availability of the deposited material from the NCMA; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

The foregoing invention has been described in detail by way of illustration and example for purposes of clarity and understanding. However, it will be apparent that certain changes and modifications may be practiced within the scope of the invention.

What is claimed is:

1. A seed of tetraploid watermelon line 54WA016, a representative sample of seed having been deposited under NCMA Accession No. 202411027.

2. A plant of tetraploid watermelon line 54WA016, a representative sample of seed having been deposited under NCMA Accession No. 202411027.

3. A watermelon plant, or a part thereof, having all the physiological and morphological characteristics of the watermelon plant of claim 2.

4. A seed that produces the plant of claim 3.

5. A plant part of the plant of claim 2.

6. The plant part of claim 5, wherein the plant part is a fruit, a scion, a rootstock, a shoot, pollen, an ovule, an anther, a root, root tip, or a cell.

7. An F1 seed of the plant of claim 2.

8. The seed of claim 7, wherein the seed is triploid.

9. The seed of claim 7, wherein the seed is tetraploid.

10. A tissue culture of regenerable cells of the watermelon plant of claim 2.

11. A single locus converted watermelon plant, comprising a single locus conversion and otherwise comprising all of the physiological and morphological characteristics of watermelon line 54WA016, a representative sample of seed having been deposited under NCMA Accession No. 202411027.

12. A seed that produces the plant of claim 11.

13. A grafted watermelon plant comprising a rootstock and a scion, wherein the plant of claim 2 is used as the scion and the rootstock is from a different watermelon plant.

14. A method of producing a grafted watermelon plant, the method comprising:

(a) providing a scion from the plant of claim 2; and (b) grafting the scion to a rootstock from a different watermelon plant.

15. A method of producing watermelon seed, the method comprising crossing the plant of claim 2 with itself or a second watermelon plant and harvesting the resulting seed.

16. An F1 watermelon seed produced by the method of claim 15.

17. A watermelon plant, or a fruit thereof, produced by growing the seed of claim 16.

18. A method for producing a seed of a watermelon plant derived from the plant of claim 2, the method comprising:

(a) crossing a plant of watermelon line 54WA016 with a second watermelon plant; and (b) allowing seed to form;

(c) growing a plant from the seed of step (b) to produce a plant derived from watermelon line 54WA016;

(d) selfing the plant of step (c) or crossing it to a second watermelon plant to form additional watermelon seed derived from watermelon line 54WA016; and (e) optionally repeating steps (c) and (d) one or more times to generate further derived watermelon seed from watermelon line 54WA016, wherein in step (c) a plant is grown from the additional watermelon seed of step (d) in place of growing a plant from the seed of step (b).

19. A method of vegetatively propagating the plant of claim 2, the method comprising:

(a) collecting tissue capable of being propagated from a plant of watermelon line 54WA016;

(b) cultivating the tissue to obtain proliferated shoots; and (c) rooting the proliferated shoots to obtain rooted plantlets.

20. The method of claim 19, wherein the method further comprises growing plants from the rooted plantlets.

21. A method of introducing a desired added trait into watermelon line 54WA016, the method comprising:

(a) crossing the plant of claim 2 with a watermelon plant that comprises a desired added trait to produce F1 progeny;

(b) selecting an F1 progeny that comprises the desired added trait;

(c) crossing the selected F1 progeny with watermelon line 54WA016 to produce backcross progeny;

(d) selecting a backcross progeny comprising the desired added trait; and (e) optionally repeating steps (c) and (d) three or more times to produce a plant derived from watermelon line 54WA016 comprising a desired added trait and otherwise all of the physiological and morphological characteristics of watermelon line 54WA016, wherein in step (c) the selected backcross progeny produced in step (d) is used in place of the selected F1 progeny of step (b).

22. The method of claim 21, wherein the desired added trait is male sterility, pest resistance, insect resistance, disease resistance, herbicide resistance, or any combination thereof.

23. A watermelon plant produced by the method of claim 21, wherein said watermelon plant comprises the desired added trait and otherwise all of the physiological and morphological characteristics of watermelon line 54WA016.

24. A seed that produces the plant of claim 23.

25. A method of producing a plant of watermelon line 54WA016 comprising a desired added trait, the method comprising introducing a transgene conferring the desired trait into the plant of claim 2, wherein the plant comprises the desired added trait and otherwise all of the physiological and morphological characteristics of watermelon line 54WA016.

26. A watermelon plant produced by the method of claim 25, wherein said watermelon plant comprises the transgene and has the desired added trait and otherwise has all of the physiological and morphological characteristics of watermelon line 54WA016.

27. A seed that produces the plant of claim 26, wherein the seed produces a plant that has the desired added trait and otherwise all of the physiological and morphological characteristics of watermelon line 54WA016.

28. A method of producing triploid watermelon seed, the method comprising:

(a) crossing the watermelon plant of claim 2 with a diploid watermelon plant; and (b) harvesting the resultant triploid watermelon seed.

29. An F1 triploid watermelon seed produced by the method of claim 28.

30. An F1 triploid watermelon plant, or fruit thereof, produced from the seed of claim 29.

31. A method of producing seedless watermelon fruit, the method comprising:

(a) crossing the triploid plant of claim 30 and a diploid watermelon plant;

(b) allowing seedless fruit to form; and (c) harvesting the seedless fruit.

32. A seedless watermelon fruit produced by the method of claim 31.

33. A method of producing tetraploid watermelon seed, the method comprising crossing the plant of claim 2 with itself or a different tetraploid watermelon plant and harvesting the seed.

34. An F1 tetraploid watermelon seed produced by the method of claim 33.

35. An F1 tetraploid watermelon plant, or a fruit thereof, grown from the seed of claim 34.

36. A method of determining a genotype of watermelon line 54WA016, the method comprising:

(a) obtaining a sample of nucleic acids from the plant of claim 2; and (b) detecting a polymorphism in the nucleic acid sample.

* * * * *